(12) United States Patent
Thomas et al.

(10) Patent No.: US 7,910,795 B2
(45) Date of Patent: Mar. 22, 2011

(54) ABSORBENT ARTICLE CONTAINING A CROSSLINKED ELASTIC FILM

(75) Inventors: Oomman P. Thomas, Alpharetta, GA (US); C. Allen Smith, Cumming, GA (US); James Austin, Johns Creek, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 1047 days.

(21) Appl. No.: 11/716,406

(22) Filed: Mar. 9, 2007

(65) Prior Publication Data

US 2008/0221540 A1    Sep. 11, 2008

(51) Int. Cl.
C08F 2/46 (2006.01)
C08J 3/28 (2006.01)
A61L 15/00 (2006.01)

(52) U.S. Cl. ............ 604/358; 604/385.23; 604/385.27; 604/385.24; 522/150; 522/153; 522/155; 522/157; 522/159; 522/161; 522/111; 522/112; 428/221; 428/323; 428/409; 428/500; 264/405; 264/424; 264/425; 264/464; 264/470; 264/477

(58) Field of Classification Search .................. 522/150, 522/153, 155, 157, 158, 159, 161, 109, 110, 522/111, 113; 264/405, 424, 425, 464, 470, 264/477; 428/221, 323, 409, 500; 604/358, 604/385.23, 385.27, 385.24

See application file for complete search history.

(56) References Cited

U.S. PATENT DOCUMENTS

| | | | |
|---|---|---|---|
| 3,086,242 A | 4/1963 | Cook et al. | |
| 3,338,992 A | 8/1967 | Kinney | |
| 3,341,394 A | 9/1967 | Kinney | |
| 3,354,506 A | 11/1967 | Raley | |
| 3,494,821 A | 2/1970 | Evans | |
| 3,502,538 A | 3/1970 | Petersen | |
| 3,502,763 A | 3/1970 | Hartmann | |
| 3,542,615 A | 11/1970 | Dobo et al. | |
| 3,639,917 A | 2/1972 | Althouse | |
| 3,650,649 A | 3/1972 | Schippers | |
| 3,692,618 A | 9/1972 | Dorschner et al. | |
| 3,801,429 A | 4/1974 | Schrenk et al. | |
| 3,802,817 A | 4/1974 | Matsuki et al. | |
| 3,849,241 A | 11/1974 | Butin et al. | |
| 3,912,565 A | 10/1975 | Koch et al. | |
| RE28,688 E | 1/1976 | Cook | |
| 4,041,203 A | 8/1977 | Brock et al. | |
| 4,144,370 A | 3/1979 | Boulton | |
| 4,323,534 A | 4/1982 | DesMarais | |
| 4,340,563 A | 7/1982 | Appel et al. | |
| 4,374,888 A | 2/1983 | Bornslaeger | |
| 4,543,154 A | 9/1985 | Reiter | |
| 4,552,795 A | 11/1985 | Hansen et al. | |
| 4,640,726 A | 2/1987 | Sallee et al. | |
| 4,640,859 A | 2/1987 | Hansen et al. | |
| 4,663,106 A | 5/1987 | Pomplun et al. | |
| 4,663,220 A | 5/1987 | Wisneski et al. | |
| 4,665,306 A | 5/1987 | Roland et al. | |
| 4,680,450 A | 7/1987 | Thorson et al. | |
| 4,704,116 A | 11/1987 | Enloe | |
| 4,720,415 A | 1/1988 | Vander Wielen et al. | |
| 4,766,029 A | 8/1988 | Brock et al. | |
| 4,787,699 A | 11/1988 | Moulin | |
| 4,789,592 A | 12/1988 | Taniguchi et al. | |
| 4,795,668 A | 1/1989 | Krueger et al. | |
| 4,798,603 A | 1/1989 | Meyer et al. | |
| 4,816,094 A | 3/1989 | Pomplun et al. | |
| 4,834,738 A | 5/1989 | Kielpikowski et al. | |
| 4,861,652 A * | 8/1989 | Lippert et al. | 428/152 |
| 4,916,005 A | 4/1990 | Lippert et al. | |
| 4,937,299 A | 6/1990 | Ewen et al. | |
| 4,940,464 A | 7/1990 | Van Gompel et al. | |
| 4,965,122 A | 10/1990 | Morman | |
| 4,981,747 A | 1/1991 | Morman | |
| 5,003,178 A | 3/1991 | Livesay | |
| 5,057,368 A | 10/1991 | Largman et al. | |
| 5,069,970 A | 12/1991 | Largman et al. | |
| 5,093,422 A | 3/1992 | Himes | |
| 5,108,820 A | 4/1992 | Kaneko et al. | |
| 5,140,757 A | 8/1992 | Terada | |

(Continued)

FOREIGN PATENT DOCUMENTS

| | | |
|---|---|---|
| EP | 1184014 A2 | 3/2002 |
| WO | WO 9516425 A1 | 6/1995 |
| WO | WO 0039201 | 7/2000 |

(Continued)

OTHER PUBLICATIONS

Search Report and Written Opinion for PCT/IB2007/051132, Oct. 2, 2007.
Product Data Sheet—EXACT 5361 Plastomer for Polymer Modification—Exxon Mobil Chemical.
ASTM D 5035-95, *Breaking Force and Elongation of Textile Fabrics (Strip Method)*.
ASTM D 3418-03, *Transition Temperatures and Enthalpies of Fusion and Crystallization of Polymers by Differential Scanning Calorimetry*.
ASTM D 1525-07, *Vicat Softening Temperature of Plastics*.

(Continued)

*Primary Examiner* — Sanza L McClendon
(74) *Attorney, Agent, or Firm* — Dority & Manning, P.A.

(57) ABSTRACT

A technique for imparting latent elasticity to components of an absorbent article is provided. More specifically, a latent elastic film that contains a crosslinkable semi-crystalline polyolefin is initially incorporated into an absorbent article. The film is not highly elastic prior to crosslinking and is thus dimensionally stable. Consequently, the film need not be maintained in a mechanically stretched condition during attachment to other components of the absorbent article, which provides for greater freedom in the location and manner in which the components are attached together. Once incorporated into the absorbent article, the semi-crystalline polyolefin is crosslinked to form a three-dimensional network having elastic memory. The film may also be heat activated, either through crosslinking or an additional step, to cause the film to shrink and further improve its stretch characteristics.

38 Claims, 1 Drawing Sheet

U.S. PATENT DOCUMENTS

| | | | |
|---|---|---|---|
| 5,162,074 A | 11/1992 | Hills | |
| 5,169,706 A | 12/1992 | Collier, IV et al. | |
| 5,176,668 A | 1/1993 | Bernardin | |
| 5,176,672 A | 1/1993 | Bruemmer et al. | |
| 5,192,606 A | 3/1993 | Proxmire et al. | |
| 5,213,881 A | 5/1993 | Timmons et al. | |
| 5,218,071 A | 6/1993 | Tsutsui et al. | |
| 5,226,992 A | 7/1993 | Morman | |
| 5,272,236 A | 12/1993 | Lai et al. | |
| 5,277,976 A | 1/1994 | Hogle et al. | |
| 5,278,272 A | 1/1994 | Lai et al. | |
| 5,284,703 A | 2/1994 | Everhart et al. | |
| 5,304,599 A | 4/1994 | Himes | |
| 5,322,728 A | 6/1994 | Davey et al. | |
| 5,332,613 A | 7/1994 | Taylor et al. | |
| 5,336,545 A | 8/1994 | Morman | |
| 5,336,552 A | 8/1994 | Strack et al. | |
| 5,340,431 A | 8/1994 | Terada | |
| 5,359,525 A * | 10/1994 | Weyenberg | 700/124 |
| 5,368,666 A | 11/1994 | Terada | |
| 5,382,400 A | 1/1995 | Pike et al. | |
| 5,385,775 A | 1/1995 | Wright | |
| 5,399,219 A | 3/1995 | Roessler et al. | |
| 5,429,856 A | 7/1995 | Krueger et al. | |
| 5,464,688 A | 11/1995 | Timmons et al. | |
| 5,466,410 A | 11/1995 | Hills | |
| 5,472,775 A | 12/1995 | Obijeski et al. | |
| 5,486,166 A | 1/1996 | Bishop et al. | |
| 5,490,846 A | 2/1996 | Ellis et al. | |
| 5,501,679 A | 3/1996 | Krueger et al. | |
| 5,509,915 A | 4/1996 | Hanson et al. | |
| 5,539,056 A | 7/1996 | Yang et al. | |
| 5,540,796 A | 7/1996 | Fries | |
| 5,571,619 A | 11/1996 | McAlpin et al. | |
| 5,595,618 A | 1/1997 | Fries et al. | |
| 5,596,052 A | 1/1997 | Resconi et al. | |
| 5,620,780 A | 4/1997 | Krueger et al. | |
| 5,649,916 A | 7/1997 | DiPalma et al. | |
| 5,691,034 A | 11/1997 | Krueger et al. | |
| 5,766,389 A | 6/1998 | Brandon et al. | |
| 5,773,374 A | 6/1998 | Wood et al. | |
| 5,800,903 A | 9/1998 | Wood et al. | |
| 5,827,259 A | 10/1998 | Laux et al. | |
| 5,840,412 A | 11/1998 | Wood et al. | |
| 5,885,908 A | 3/1999 | Jaeger et al. | |
| 5,932,497 A | 8/1999 | Morman et al. | |
| H1808 H | 10/1999 | Djiauw et al. | |
| 5,997,981 A | 12/1999 | McCormack et al. | |
| 6,015,764 A | 1/2000 | McCormack et al. | |
| 6,060,009 A | 5/2000 | Welygan et al. | |
| 6,090,325 A | 7/2000 | Wheat et al. | |
| 6,110,158 A | 8/2000 | Kielpikowski | |
| 6,111,163 A | 8/2000 | McCormack et al. | |
| 6,200,669 B1 | 3/2001 | Marmon et al. | |
| 6,315,864 B2 | 11/2001 | Anderson et al. | |
| 6,402,729 B1 * | 6/2002 | Boberg et al. | 604/385.28 |
| 6,407,492 B1 | 6/2002 | Avnery et al. | |
| 6,436,529 B1 | 8/2002 | Deeb et al. | |
| 6,461,457 B1 | 10/2002 | Taylor et al. | |
| 6,479,154 B1 | 11/2002 | Walton et al. | |
| 6,500,563 B1 | 12/2002 | Datta et al. | |
| 6,565,549 B1 * | 5/2003 | Allen et al. | 604/385.04 |
| 6,645,190 B1 | 11/2003 | Olson et al. | |
| 6,663,611 B2 | 12/2003 | Blaney et al. | |
| 6,667,351 B2 | 12/2003 | Langohr et al. | |
| H2096 H | 1/2004 | Erderly et al. | |
| 6,709,742 B2 | 3/2004 | Ladika et al. | |
| 6,719,744 B2 * | 4/2004 | Kinnear et al. | 604/389 |
| 6,736,917 B2 | 5/2004 | Tange | |
| 6,761,711 B1 | 7/2004 | Fletcher et al. | |
| 6,794,024 B1 | 9/2004 | Walton et al. | |
| 6,815,864 B2 | 11/2004 | Tanaka et al. | |
| 6,824,734 B2 | 11/2004 | Boggs et al. | |
| 6,861,135 B2 * | 3/2005 | Zhou | 428/323 |
| 6,902,796 B2 | 6/2005 | Morell et al. | |
| 6,916,750 B2 | 7/2005 | Thomas et al. | |
| 6,933,421 B2 * | 8/2005 | Topolkaraev et al. | 604/361 |
| 6,946,413 B2 | 9/2005 | Lange et al. | |
| 6,964,720 B2 | 11/2005 | Schneider et al. | |
| 7,074,484 B2 * | 7/2006 | Topolkaraev et al. | 428/411.1 |
| 7,189,888 B2 * | 3/2007 | Wang et al. | 604/367 |
| 7,384,491 B2 * | 6/2008 | Fitts et al. | 156/169 |
| 7,445,831 B2 * | 11/2008 | Ashraf et al. | 428/138 |
| 7,491,666 B2 * | 2/2009 | Smith et al. | 442/366 |
| 7,582,178 B2 * | 9/2009 | Hughes et al. | 156/229 |
| 7,585,382 B2 * | 9/2009 | Hughes et al. | 156/244.11 |
| 2002/0009940 A1 | 1/2002 | May et al. | |
| 2002/0049269 A1 | 4/2002 | Ho et al. | |
| 2002/0104608 A1 | 8/2002 | Welch et al. | |
| 2003/0068951 A1 | 4/2003 | Boggs et al. | |
| 2004/0006324 A1 | 1/2004 | Zhou et al. | |
| 2004/0110442 A1 | 6/2004 | Rhim et al. | |
| 2004/0121687 A1 | 6/2004 | Morman et al. | |
| 2004/0127131 A1 | 7/2004 | Potnis | |
| 2005/0043460 A1 | 2/2005 | McCormack et al. | |
| 2005/0148263 A1 | 7/2005 | Zhou et al. | |
| 2005/0170729 A1 | 8/2005 | Stadelman et al. | |
| 2005/0215973 A1 * | 9/2005 | Roe et al. | 604/385.29 |
| 2005/0245162 A1 | 11/2005 | McCormack et al. | |
| 2006/0003658 A1 | 1/2006 | Hall et al. | |
| 2006/0055089 A1 | 3/2006 | Zhang et al. | |
| 2006/0131783 A1 | 6/2006 | Morman et al. | |
| 2006/0135024 A1 | 6/2006 | Thomas et al. | |
| 2006/0148358 A1 | 7/2006 | Hall et al. | |
| 2006/0151914 A1 | 7/2006 | Gerndt et al. | |
| 2006/0246803 A1 | 11/2006 | Smith et al. | |
| 2006/0251858 A1 | 11/2006 | Thomas et al. | |
| 2007/0044905 A1 * | 3/2007 | Fitts et al. | 156/244.11 |

FOREIGN PATENT DOCUMENTS

| | | |
|---|---|---|
| WO | WO 0132116 A1 | 5/2001 |
| WO | WO 03031151 A1 | 4/2003 |
| WO | WO 03040442 A1 | 5/2003 |
| WO | WO 2004 020174 A1 | 3/2004 |
| WO | WO 2005021262 A1 | 3/2005 |
| WO | WO 2005110719 A1 | 11/2005 |

OTHER PUBLICATIONS

ASTM D 1505-03, *Density of Plastics by the Density-Gradient Technique*.
ASTM E 96-80, *Water Vapor Transmission of Materials*.
ASTM D 1238-01, *Melt Flow Rates of Thermoplastics by Extrusion Plastometer*.
ASTM D 2838-02, *Shrink Tension and Orientation Release Stress of Plastic Film and Thin Sheeting*.

\* cited by examiner

ABSORBENT ARTICLE CONTAINING A CROSSLINKED ELASTIC FILM

BACKGROUND OF THE INVENTION

Elastic films are commonly incorporated into products (e.g., diapers, training pants, garments, etc.) to improve their ability to better fit the contours of the body. For example, an elastic composite may be formed from the elastic film and one or more nonwoven web facings. The nonwoven web facing may be joined to the elastic film while the film is in a stretched condition so that the nonwoven web facing can gather between the locations where it is bonded to the film when it is relaxed. The resulting elastic composite is stretchable to the extent that the nonwoven web facing gathered between the bond locations allows the elastic film to elongate. Examples of stretch bonded composites are disclosed, for example, in U.S. Pat. No. 4,720,415 to Vander Wielen et al. Unfortunately, however, the stretchable nature of the composites may cause problems during the manufacturing process of the ultimate products. For example, the force required to unwind the rolled composites may at least partially extend the elastic composite while the elastic article is in tension. This partial extension of the stretchable composite can make it difficult to properly measure and position the desired quantity of the elastic article in the final product.

As such, a need exists for materials that remain relatively inelastic prior to incorporation into a final product, but which achieve a certain level of elasticity after having been activated in the final product.

SUMMARY OF THE INVENTION

In accordance with one embodiment of the present invention, a method of forming an absorbent article is disclosed. The method comprises fastening a latent elastic film to one or more components of the article. The latent elastic film comprises at least one crosslinkable semi-crystalline polyolefin having a density of about 0.91 grams per cubic centimeter or less, the semi-crystalline polyolefin constituting about 30 wt. % or more of the polymer content of the film. Thereafter, the absorbent article is subjected to a dosage of electromagnetic radiation sufficient to crosslink the semi-crystalline polyolefin. The crosslinked semi-crystalline polyolefin is elastic.

In accordance with another embodiment of the present invention, a method of forming an absorbent article that includes an absorbent core positioned between a substantially liquid-impermeable layer and a liquid-permeable layer is disclosed. The method comprises fastening a latent elastic film to one or more components of the article. The latent elastic film comprises at least one crosslinkable ethylene/α-olefin copolymer having a density of about 0.91 grams per cubic centimeter or less, the ethylene/α-olefin copolymer constituting about 30 wt. % or more of the polymer content of the film. The latent elastic film is heated at a temperature of from about 50° C. to about 100° C. The absorbent article is subjected to electromagnetic radiation at a dosage of about 3 to about 25 Megarads to crosslink the ethylene/α-olefin copolymer. The crosslinked ethylene/α-olefin copolymer is elastic.

Other features and aspects of the present invention are described in more detail below.

BRIEF DESCRIPTION OF THE DRAWINGS

A full and enabling disclosure of the present invention, including the best mode thereof, directed to one of ordinary skill in the art, is set forth more particularly in the remainder of the specification, which makes reference to the appended FIGURE in which.

Figure 1:
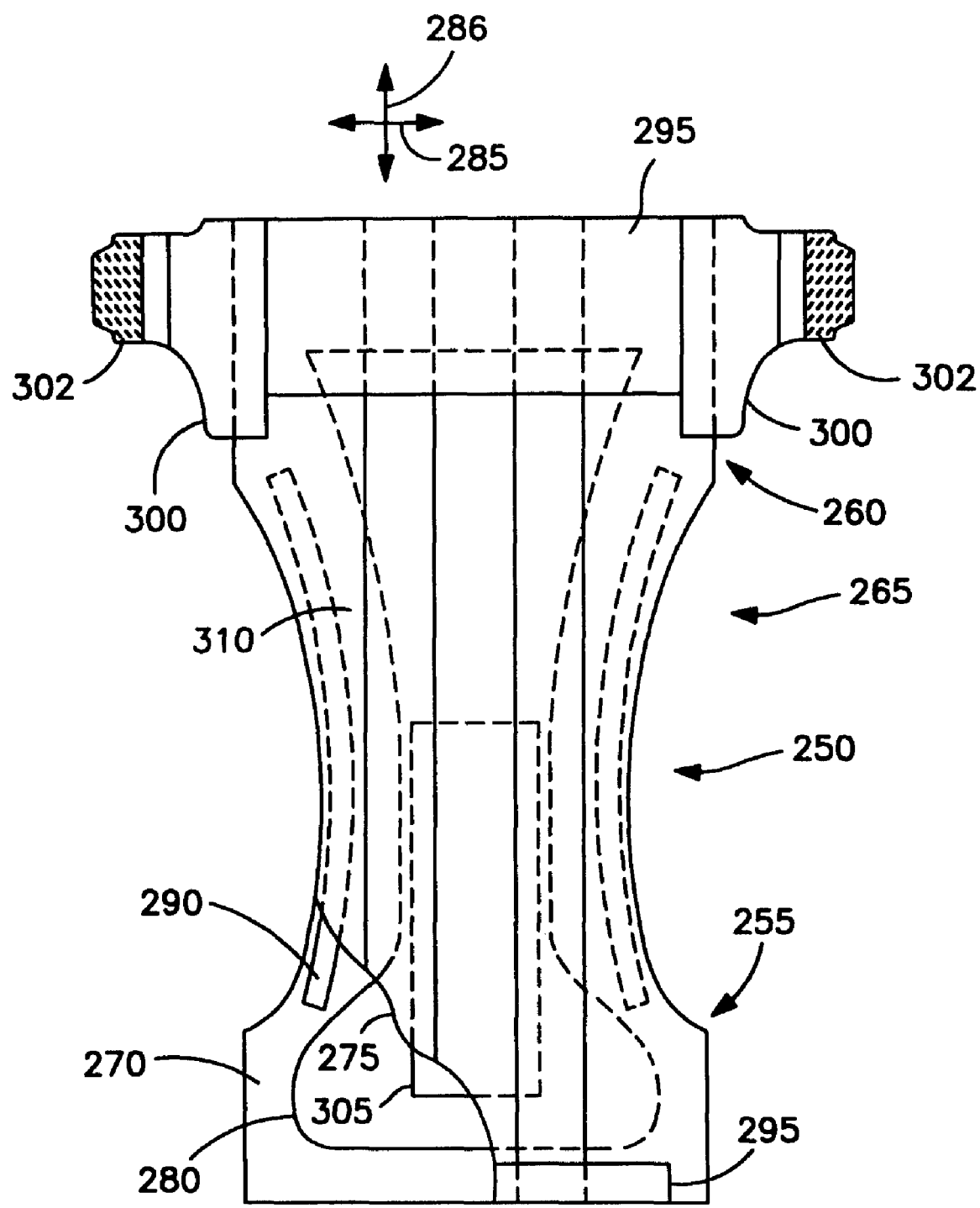
FIG. 1 is a perspective view of an absorbent article that may be formed in accordance with one embodiment of the present invention.

Repeat use of reference characters in the present specification and drawing is intended to represent same or analogous features or elements of the invention.

DETAILED DESCRIPTION OF REPRESENTATIVE EMBODIMENTS

Definitions

As used herein, the term "absorbent article" generally refers to any article capable of absorbing water or other fluids. Examples of some absorbent articles include, but are not limited to, personal care absorbent articles, such as diapers, training pants, absorbent underpants, incontinence articles, feminine hygiene products (e.g., sanitary napkins), swim wear, baby wipes, and so forth; medical absorbent articles, such as garments, fenestration materials, underpads, bedpads, bandages, absorbent drapes, and medical wipes; food service wipers; clothing articles; and so forth. Materials and processes suitable for forming such absorbent articles are well known to those skilled in the art.

As used herein, the term "nonwoven web" generally refers to a web having a structure of individual fibers or threads which are interlaid, but not in an identifiable manner as in a knitted fabric. Examples of suitable nonwoven fabrics or webs include, but are not limited to, meltblown webs, spunbond webs, carded webs, etc. The basis weight of the nonwoven web may generally vary, such as from about 0.1 grams per square meter ("gsm") to 120 gsm, in some embodiments from about 0.5 gsm to about 70 gsm, and in some embodiments, from about 1 gsm to about 35 gsm.

As used herein, the term "meltblown web" generally refers to a nonwoven web that is formed by a process in which a molten thermoplastic material is extruded through a plurality of fine, usually circular, die capillaries as molten fibers into converging high velocity gas (e.g. air) streams that attenuate the fibers of molten thermoplastic material to reduce their diameter, which may be to microfiber diameter. Thereafter, the meltblown fibers are carried by the high velocity gas stream and are deposited on a collecting surface to form a web of randomly dispersed meltblown fibers. Such a process is disclosed, for example, in U.S. Pat. No. 3,849,241 to Butin, et al., which is incorporated herein in its entirety by reference thereto for all purposes. Generally speaking, meltblown fibers may be microfibers that are substantially continuous or discontinuous, generally smaller than 10 microns in diameter, and generally tacky when deposited onto a collecting surface.

As used herein, the term "spunbond web" generally refers to a web containing small diameter substantially continuous fibers. The fibers are formed by extruding a molten thermoplastic material from a plurality of fine, usually circular, capillaries of a spinnerette with the diameter of the extruded fibers then being rapidly reduced as by, for example, eductive drawing and/or other well-known spunbonding mechanisms. The production of spunbond webs is described and illustrated, for example, in U.S. Pat. No. 4,340,563 to Appel, et al., U.S. Pat. No. 3,692,618 to Dorschner, et al., U.S. Pat. No. 3,802,817 to Matsuki, et al., U.S. Pat. No. 3,338,992 to Kinney, U.S. Pat. No. 3,341,394 to Kinney, U.S. Pat. No. 3,502,763 to Hartman, U.S. Pat. No. 3,502,538 to Levy, U.S. Pat. No. 3,542,615 to Dobo, et al., and U.S. Pat. No. 5,382,400 to Pike, et al., which are incorporated herein in their entirety by reference thereto for all purposes. Spunbond fibers are generally not tacky when they are deposited onto a collecting surface. Spunbond fibers may sometimes have diameters less than about 40 microns, and are often between about 5 to about 20 microns.

As used herein, the terms "machine direction" or "MD" generally refers to the direction in which a material is produced. The term "cross-machine direction" or "CD" refers to the direction perpendicular to the machine direction. Dimensions measured in the cross-machine direction are referred to as "width" dimension, while dimensions measured in the machine direction are referred to as "length" dimensions.

As used herein, the term "elastomeric" and "elastic" and refers to a material that, upon application of a stretching force, is stretchable in at least one direction (such as the CD direction), and which upon release of the stretching force, contracts/returns to approximately its original dimension. For example, a stretched material may have a stretched length that is at least 50% greater than its relaxed unstretched length, and which will recover to within at least 50% of its stretched length upon release of the stretching force. A hypothetical example would be a one (1) inch sample of a material that is stretchable to at least 1.50 inches and which, upon release of the stretching force, will recover to a length of not more than 1.25 inches. Desirably, the material contracts or recovers at least 50%, and even more desirably, at least 80% of the stretched length.

As used herein the terms "extensible" or "extensibility" generally refers to a material that stretches or extends in the direction of an applied force by at least about 50% of its relaxed length or width. An extensible material does not necessarily have recovery properties. For example, an elastomeric material is an extensible material having recovery properties. A meltblown web may be extensible, but not have recovery properties, and thus, be an extensible, non-elastic material.

As used herein, the term "percent stretch" refers to the degree to which a material stretches in a given direction when subjected to a certain force. In particular, percent stretch is determined by measuring the increase in length of the material in the stretched dimension, dividing that value by the original dimension of the material, and then multiplying by 100. Such measurements are determined using the "strip elongation test", which is substantially in accordance with the specifications of ASTM D5035-95. Specifically, the test uses two clamps, each having two jaws with each jaw having a facing in contact with the sample. The clamps hold the material in the same plane, usually vertically, separated by 3 inches and move apart at a specified rate of extension. The sample size is 3 inches by 6 inches, with a jaw facing height of 1 inch and width of 3 inches, and a constant rate of extension of 300 mm/min. The specimen is clamped in, for example, a Sintech 2/S tester with a Renew MTS mongoose box (control) and using TESTWORKS 4.07b software (Sintech Corp, of Cary, N.C.). The test is conducted under ambient conditions. Results are generally reported as an average of three specimens and may be performed with the specimen in the cross direction (CD) and/or the machine direction (MD).

DETAILED DESCRIPTION

Reference now will be made in detail to various embodiments of the invention, one or more examples of which are set forth below. Each example is provided by way of explanation, not limitation of the invention. In fact, it will be apparent to those skilled in the art that various modifications and variations may be made in the present invention without departing from the scope or spirit of the invention. For instance, features illustrated or described as part of one embodiment, may be used on another embodiment to yield a still further embodiment. Thus, it is intended that the present invention cover such modifications and variations.

Generally speaking, the present invention is directed to a technique for imparting latent elasticity to components of an absorbent article. More specifically, a latent elastic film that contains a crosslinkable semi-crystalline polyolefin is initially incorporated into an absorbent article. The film is not highly elastic prior to crosslinking and is thus dimensionally stable. Consequently, the film need not be maintained in a mechanically stretched condition during attachment to other components of the absorbent article, which provides for greater freedom in the location and manner in which the components are attached together. Once incorporated into the absorbent article, the semi-crystalline polyolefin is crosslinked to form a three-dimensional network having elastic memory. The film may also be heat activated, either through crosslinking or an additional step, to cause the film to shrink and further improve its stretch characteristics.

I. Latent Elastic Film

The latent elastic film of the present invention contains a crosslinkable polyolefin that has or is capable of exhibiting a substantially regular structure ("semi-crystalline"). Such semi-crystalline polyolefins may be substantially amorphous in their undeformed state, but form crystalline domains upon stretching. The degree of crystallinity of the olefin polymer may be from about 3% to about 30%, in some embodiments from about 5% to about 25%, and in some embodiments, from about 5% and about 15%. Likewise, the semi-crystalline polyolefin may have a latent heat of fusion ($\Delta H_f$), which is another indicator of the degree of crystallinity, of from about 15 to about 75 Joules per gram ("J/g"), in some embodiments from about 20 to about 65 J/g, and in some embodiments, from 25 to about 50 J/g. The semi-crystalline polyolefin may also have a Vicat softening temperature of from about 10° C. to about 100° C., in some embodiments from about 20° C. to about 80° C., and in some embodiments, from about 30° C. to about 60° C. The semi-crystalline polyolefin may have a melting temperature of from about 20° C. to about 120° C., in some embodiments from about 35° C. to about 90° C., and in some embodiments, from about 40° C. to about 80° C. The latent heat of fusion ($\Delta H_f$) and melting temperature may be determined using differential scanning calorimetry ("DSC") in accordance with ASTM D-3417 as is well known to those skilled in the art. The Vicat softening temperature may be determined in accordance with ASTM D-1525.

Exemplary semi-crystalline polyolefins include polyethylene, polypropylene, blends and copolymers thereof. In one particular embodiment, a polyethylene is employed that is a copolymer of ethylene and an α-olefin, such as a $C_3$-$C_{20}$ α-olefin or $C_3$-$C_{12}$ α-olefin. Suitable α-olefins may be linear or branched (e.g., one or more $C_1$-$C_3$ alkyl branches, or an aryl group). Specific examples include 1-butene; 3-methyl-1-butene; 3,3-dimethyl-1-butene; 1-pentene; 1-pentene with one or more methyl, ethyl or propyl substituents; 1-hexene with one or more methyl, ethyl or propyl substituents; 1-heptene with one or more methyl, ethyl or propyl substituents; 1-octene with one or more methyl, ethyl or propyl substituents; 1-nonene with one or more methyl, ethyl or propyl substituents; ethyl, methyl or dimethyl-substituted 1-decene; 1-dodecene; and styrene. Particularly desired α-olefin comonomers are 1-butene, 1-hexene and 1-octene. The ethylene content of such copolymers may be from about 60 mole % to about 99 mole %, in some embodiments from about 80 mole % to about 98.5 mole %, and in some embodiments, from about 87 mole % to about 97.5 mole %. The α-olefin content may likewise range from about 1 mole % to about 40 mole %, in some embodiments from about 1.5 mole % to about 15 mole %, and in some embodiments, from about 2.5 mole % to about 13 mole %.

The density of the polyethylene may vary depending on the type of polymer employed, but generally ranges from 0.85 to 0.96 grams per cubic centimeter ("g/cm$^3$"). Polyethylene "plastomers", for instance, may have a density in the range of from 0.85 to 0.91 g/cm$^3$. Likewise, "linear low density polyethylene" ("LLDPE") may have a density in the range of from 0.91 to 0.94 g/cm$^3$; "low density polyethylene" ("LDPE") may have a density in the range of from 0.91 to 0.94 g/cm$^3$; and "high density polyethylene" ("HDPE") may have density in the range of from 0.94 to 0.96 g/cm$^3$. Densities may be measured in accordance with ASTM 1505.

Particularly suitable polyethylene copolymers are those that are "linear" or "substantially linear." The term "substantially linear" means that, in addition to the short chain branches attributable to comonomer incorporation, the ethylene polymer also contains long chain branches in the polymer backbone. "Long chain branching" refers to a chain length of at least 6 carbons. Each long chain branch may have the same comonomer distribution as the polymer backbone and be as long as the polymer backbone to which it is attached. Preferred substantially linear polymers are substituted with from 0.01 long chain branch per 1000 carbons to 1 long chain branch per 1000 carbons, and in some embodiments, from 0.05 long chain branch per 1000 carbons to 1 long chain branch per 1000 carbons. In contrast to the term "substantially linear", the term "linear" means that the polymer lacks measurable or demonstrable long chain branches. That is, the polymer is substituted with an average of less than 0.01 long chain branch per 1000 carbons.

The density of a linear ethylene/α-olefin copolymer is a function of both the length and amount of the α-olefin. That is, the greater the length of the α-olefin and the greater the amount of α-olefin present, the lower the density of the copolymer. Although not necessarily required, linear polyethylene "plastomers" are particularly desirable in that the content of α-olefin short chain branching content is such that the ethylene copolymer exhibits both plastic and elastomeric characteristics—i.e., a "plastomer." Because polymerization with α-olefin comonomers decreases crystallinity and density, the resulting plastomer normally has a density lower than that of polyethylene thermoplastic polymers (e.g., LLDPE), but approaching and/or overlapping that of an elastomer. For example, the density of the polyethylene plastomer may be about 0.91 grams per cubic centimeter (g/cm$^3$) or less, in some embodiments from about 0.85 to about 0.89 g/cm$^3$, and in some embodiments, from about 0.85 g/cm$^3$ to about 0.88 g/cm$^3$. Despite having a density similar to elastomers, plastomers generally exhibit a higher degree of crystallinity, are relatively non-tacky, and may be formed into pellets that are non-adhesive and relatively free flowing.

The distribution of the α-olefin comonomer within a polyethylene plastomer is typically random and uniform among the differing molecular weight fractions forming the ethylene copolymer. This uniformity of comonomer distribution within the plastomer may be expressed as a "Comonomer Distribution Breadth Index" value ("CDBI") of 60 or more, in some embodiments 80 or more, and in some embodiments, 90 or more. Further, the polyethylene plastomer may be characterized by a DSC melting point curve that exhibits a single melting point peak in the region of 50 to 110° C. (second melt rundown).

Preferred plastomers for use in the present invention are ethylene-based copolymer plastomers available under the EXACT™ from ExxonMobil Chemical Company of Houston, Tex. Other suitable polyethylene plastomers are available under the designation ENGAGE™ and AFFINITY™ from Dow Chemical Company of Midland, Mich. Still other suitable ethylene polymers are available from The Dow Chemical Company under the designations DOWLEX™ (LLDPE) and ATTANE™ (ULDPE). Other suitable ethylene polymers are described in U.S. Pat. No. 4,937,299 to Ewen et al.; U.S. Pat. No. 5,218,071 to Tsutsui et al.; U.S. Pat. No. 5,272,236 to Lai, et al.; and U.S. Pat. No. 5,278,272 to Lai, et al., which are incorporated herein in their entirety by reference thereto for all purposes.

Of course, the present invention is by no means limited to the use of ethylene polymers. For instance, propylene polymers may also be suitable for use as a semi-crystalline polyolefin. In one particular embodiment, the semi-crystalline propylene-based polymer includes a copolymer of propylene and an α-olefin, such as a $C_2$-$C_{20}$ α-olefin or $C_2$-$C_{12}$ α-olefin. Particularly desired α-olefin comonomers are ethylene, 1-butene, 1-hexene and 1-octene. The propylene content of such copolymers may be from about 60 mole % to about 99.5 wt. %, in some embodiments from about 80 mole % to about 99 mole %, and in some embodiments, from about 85 mole % to about 98 mole %. The α-olefin content may likewise range from about 0.5 mole % to about 40 mole %, in some embodiments from about 1 mole % to about 20 mole %, and in some embodiments, from about 2 mole % to about 15 mole %. The distribution of the α-olefin comonomer is typically random and uniform among the differing molecular weight fractions forming the propylene copolymer. Although the density of the propylene-based polymer employed in the present invention may vary, it is typically about 0.91 grams per cubic centimeter (g/cm$^3$) or less, in some embodiments from about 0.85 to about 0.89 g/cm$^3$, and in some embodiments, from about 0.85 g/cm$^3$ to about 0.88 g/cm$^3$. The melt flow rate of the propylene-based polymer may also be selected within a certain range to optimize the properties of the resulting elastic material. The melt flow rate is the weight of a polymer (in grams) that may be forced through an extrusion rheometer orifice (0.0825-inch diameter) when subjected to a force of 2160 grams in 10 minutes at 230° C. Generally speaking, the melt flow rate is high enough to improve melt processability, but not so high as to adversely interfere with binding properties. Thus, in most embodiments of the present invention, the propylene-based polymer has a melt flow index of from about 0.1 to about 10 grams per 10 minutes, in some embodiments from about 0.2 to about 5 grams per 10 minutes, and in some embodiments, from about 0.5 to about 4 grams per 10 minutes, measured in accordance with ASTM Test Method D1238-E.

Suitable propylene polymers are commercially available under the designations VISTAMAXX™ from ExxonMobil Chemical Co. of Houston, Tex.; FINA™ (e.g., 8573) from Atofina Chemicals of Feluy, Belgium; TAFMER™ available from Mitsui Petrochemical Industries; and VERSIFY™ available from Dow Chemical Co. of Midland, Mich. Other examples of suitable propylene polymers are described in U.S. Pat. No. 6,500,563 to Datta, et al.; U.S. Pat. No. 5,539,056 to Yang, et al.; and U.S. Pat. No. 5,596,052 to Resconi, et al., which are incorporated herein in their entirety by reference thereto for all purposes.

Any of a variety of known techniques may generally be employed to form the semi-crystalline polyolefins. For instance, olefin polymers may be formed using a free radical or a coordination catalyst (e.g., Ziegler-Natta). Preferably, the olefin polymer is formed from a single-site coordination catalyst, such as a metallocene catalyst. Such a catalyst system produces ethylene copolymers in which the comonomer is randomly distributed within a molecular chain and uniformly distributed across the different molecular weight fractions. Metallocene-catalyzed polyolefins are described, for instance, in U.S. Pat. No. 5,571,619 to McAlpin et al.; U.S. Pat. No. 5,322,728 to Davis et al.; U.S. Pat. No. 5,472,775 to Obijeski et al.; U.S. Pat. No. 5,272,236 to Lai et al.; and U.S. Pat. No. 6,090,325 to Wheat, et al., which are incorporated herein in their entirety by reference thereto for all purposes. Examples of metallocene catalysts include bis(n-butylcyclopentadienyl)titanium dichloride, bis(n-butylcyclopentadienyl)zirconium dichloride, bis(cyclopentadienyl)scandium chloride, bis(indenyl)zirconium dichloride, bis(methylcyclopentadienyl)titanium dichloride, bis(methylcyclopentadienyl)zirconium dichloride, cobaltocene, cyclopentadienyltitanium trichloride, ferrocene, hafnocene dichloride, isopropyl(cyclopentadienyl,-1-flourenyl)zirconium dichloride, molybdocene dichloride, nickelocene, niobocene dichloride, ruthenocene, titanocene dichloride, zirconocene chloride hydride, zirconocene dichloride, and so forth. Polymers made using metallocene catalysts typically have a narrow molecular weight range. For instance, metallocene-catalyzed polymers may have polydispersity numbers ($M_w/M_n$) of below 4, controlled short chain branching distribution, and controlled isotacticity.

The melt flow index (MI) of the semi-crystalline polyolefins may generally vary, but is typically in the range of about 0.1 grams per 10 minutes to about 100 grams per 10 minutes, in some embodiments from about 0.5 grams per 10 minutes to about 30 grams per 10 minutes, and in some embodiments, about 1 to about 10 grams per 10 minutes, determined at 190° C. The melt flow index is the weight of the polymer (in grams) that may be forced through an extrusion rheometer orifice (0.0825-inch diameter) when subjected to a force of 2.16 kilograms in 10 minutes at 190° C., and may be determined in accordance with ASTM Test Method D1238-E.

In addition to semi-crystalline polyolefin(s), other polymers may also be employed in the film. For example, thermoplastic elastomeric polymers may be employed to improve the elastic characteristics of the latent elastic film, such as elastomeric polyesters, elastomeric polyurethanes, elastomeric polyamides, elastomeric copolymers, and so forth. For example, the thermoplastic elastomer may be a substantially amorphous block copolymer having at least two blocks of a monoalkenyl arene polymer separated by at least one block of a saturated conjugated diene polymer. The monoalkenyl arene blocks may include styrene and its analogues and homologues, such as alpha-methyl styrene; p-methyl styrene; p-tert-butyl styrene; 1,3 dimethyl styrene p-methyl styrene; etc., as well as other monoalkenyl polycyclic aromatic compounds, such as vinyl naphthalene; vinyl anthrycene; and so forth. Preferred monoalkenyl arenes are styrene and p-methyl styrene. The conjugated diene blocks may include homopolymers of conjugated diene monomers, copolymers of two or more conjugated dienes, and copolymers of one or more of the dienes with another monomer in which the blocks are predominantly conjugated diene units. Preferably, the conjugated dienes contain from 4 to 8 carbon atoms, such as 1,3 butadiene (butadiene); 2-methyl-1,3 butadiene; isoprene; 2,3 dimethyl-1,3 butadiene; 1,3 pentadiene (piperylene); 1,3 hexadiene; and so forth.

The amount of monoalkenyl arene (e.g., polystyrene) blocks may vary, but typically constitute from about 8 wt. % to about 55 wt. %, in some embodiments from about 10 wt. % to about 35 wt. %, and in some embodiments, from about 25 wt. % to about 35 wt. % of the copolymer. Suitable block copolymers may contain monoalkenyl arene endblocks having a number average molecular weight from about 5,000 to about 35,000 and saturated conjugated diene midblocks having a number average molecular weight from about 20,000 to about 170,000. The total number average molecular weight of the block polymer may be from about 30,000 to about 250,000.

Particularly suitable thermoplastic elastomers are available from Kraton Polymers LLC of Houston, Tex. under the trade name KRATON®. KRATON® polymers include styrene-diene block copolymers, such as styrene-butadiene, styrene-isoprene, styrene-butadiene-styrene, and styrene-isoprene-styrene. KRATON® polymers also include styrene-olefin block copolymers formed by selective hydrogenation of styrene-diene block copolymers. Examples of such styrene-olefin block copolymers include styrene-(ethylene-butylene), styrene-(ethylene-propylene), styrene-(ethylene-butylene)-styrene, styrene-(ethylene-propylene)-styrene, styrene-(ethylene-butylene)-styrene-(ethylene-butylene), styrene-(ethylene-propylene)-styrene-(ethylene-propylene), and styrene-ethylene-(ethylene-propylene)-styrene. These block copolymers may have a linear, radial or star-shaped molecular configuration. Specific KRATON® block copolymers include those sold under the brand names G 1652, G 1657, G 1730, MD6673, and MD6937. Various suitable styrenic block copolymers are described in U.S. Pat. Nos. 4,663,220, 4,323,534, 4,834,738, 5,093,422 and 5,304,599, which are hereby incorporated in their entirety by reference thereto for all purposes. Other commercially available block copolymers include the S-EP-S elastomeric copolymers available from Kuraray Company, Ltd. of Okayama, Japan, under the trade designation SEPTON®. Still other suitable copolymers include the S-I-S and S-B-S elastomeric copolymers available from Dexco Polymers of Houston, Tex. under the trade designation VECTOR®. Also suitable are polymers composed of an A-B-A-B tetrablock copolymer, such as discussed in U.S. Pat. No. 5,332,613 to Taylor, et al., which is incorporated herein in its entirety by reference thereto for all purposes. An example of such a tetrablock copolymer is a styrene-poly(ethylene-propylene)-styrene-poly(ethylene-propylene) ("S-EP-S-EP") block copolymer.

Other exemplary thermoplastic elastomers that may be used include polyurethane elastomeric materials such as, for example, those available under the trademark ESTANE from Noveon and LYCRA from Invista, polyamide elastomeric materials such as, for example, those available under the trademark PEBAX (polyether amide) from Atofina Chemicals Inc., of Philadelphia, Pa., and polyester elastomeric materials such as, for example, those available under the trade designation HYTREL from E.I. DuPont De Nemours & Company.

The amount of semi-crystalline polyolefin(s) employed in the latent elastic film may vary, but is typically about 30 wt. % or more, in some embodiments about 50 wt. % or more, and in some embodiments, about 75 wt. % or more of the polymer content of the film. As stated, blends of semi-crystalline polyolefin(s) and other polymers (e.g., elastomeric block copolymers) may be employed. In such embodiments, the semi-crystalline polyolefin(s) typically constitute from about 30 wt. % to about 99 wt. %, in some embodiments from about 50 wt. % to about 98 wt. %, and in some embodiments, from about 75 wt. % to about 95 wt. % of the blend. The additional polymer(s) may likewise constitute from about 1 wt. % to about 70 wt. %, in some embodiments from about 2 wt. % to about 50 wt. %, and in some embodiments, from about 5 wt. % to about 25 wt. % of the blend. It should of course be understood that other elastomeric and/or non-elastomeric polymers may also be employed in the film.

Besides polymers, the latent elastic film of the present invention may also contain other components as is known in the art. In one embodiment, for example, the film contains a filler. Fillers are particulates or other forms of material that may be added to the film polymer extrusion blend and that will not chemically interfere with the extruded film, but which may be uniformly dispersed throughout the film. Fillers may serve a variety of purposes, including enhancing film opacity and/or breathability (i.e., vapor-permeable and substantially liquid-impermeable). For instance, filled films may be made breathable by stretching, which causes the polymer to break away from the filler and create microporous passageways. Breathable microporous elastic films are described, for example, in U.S. Pat. Nos. 5,997,981; 6,015,764; and 6,111,163 to McCormack, et al.; U.S. Pat. No. 5,932,497 to Morman, et al.; U.S. Pat. No. 6,461,457 to Taylor, et al., which are incorporated herein in their entirety by reference thereto for all purposes.

The fillers may have a spherical or non-spherical shape with average particle sizes in the range of from about 0.1 to about 7 microns. Examples of suitable fillers include, but are not limited to, calcium carbonate, various kinds of clay, silica, alumina, barium carbonate, sodium carbonate, magnesium carbonate, talc, barium sulfate, magnesium sulfate, aluminum sulfate, titanium dioxide, zeolites, cellulose-type powders, kaolin, mica, carbon, calcium oxide, magnesium oxide, aluminum hydroxide, pulp powder, wood powder, cellulose derivatives, chitin and chitin derivatives. A suitable coating, such as stearic acid, may also be applied to the filler particles if desired. When utilized, the filler content may vary, such as from about 25 wt. % to about 75 wt. %, in some embodiments, from about 30 wt. % to about 70 wt. %, and in some embodiments, from about 40 wt. % to about 60 wt. % of the film.

Other additives may also be incorporated into the latent elastic film, such as crosslinking catalysts, pro-rad additives, melt stabilizers, processing stabilizers, heat stabilizers, light stabilizers, antioxidants, heat aging stabilizers, whitening agents, antiblocking agents, bonding agents, tackifiers, viscosity modifiers, etc. Suitable crosslinking catalysts, for instance, may include organic bases, carboxylic acids, and organometallic compounds, such as organic titanates and complexes or carboxylates of lead, cobalt, iron, nickel, zinc and tin (e.g., dibutyltindilaurate, dioctyltinmaleate, dibutyltindiacetate, dibutyltindioctoate, stannous acetate, stannous octoate, lead naphthenate, zinc caprylate, cobalt naphthenate; etc.). Suitable pro-rad additives may likewise include azo compounds, organic peroxides and polyfunctional vinyl or allyl compounds such as, triallyl cyanurate, triallyl isocyanurate, pentaerthritol tetramethacrylate, glutaraldehyde, polyester acrylate oligomers (e.g., available from Sartomer under the designation CN2303), ethylene glycol dimethacrylate, diallyl maleate, dipropargyl maleate, dipropargyl monoallyl cyanurate, dicumyl peroxide, di-tert-butyl peroxide, t-butyl perbenzoate, benzoyl peroxide, cumene hydroperoxide, t-butyl peroctoate, methyl ethyl ketone peroxide, 2,5-dimethyl-2,5-di(t-butyl peroxy)hexane, lauryl peroxide, tert-butyl peracetate, azobisisobutyl nitrite, etc. When employed, such components may be present in any amount sufficient to impart the desired effect, such as from about 0.001 wt. % to about 25 wt. %, in some embodiments, from about 0.005 wt. % to about 10 wt. %, and in some embodiments, from 0.01 wt. % to about 5 wt. % of the film.

The latent elastic film of the present invention may be mono- or multi-layered. Multilayer films may be prepared by co-extrusion of the layers, extrusion coating, or by any conventional layering process. Such multilayer films normally contain at least one base layer and at least one skin layer, but may contain any number of layers desired. For example, the multilayer film may be formed from a base layer and one or more skin layers, wherein the base layer is formed from a semi-crystalline polyolefin in accordance with the present invention. In such embodiments, the skin layer(s) may be formed from any film-forming polymer. If desired, the skin layer(s) may contain a softer, lower melting polymer or polymer blend that renders the layer(s) more suitable as heat seal bonding layers for thermally bonding the film to a facing. In most embodiments, the skin layer(s) are formed from an olefin polymer such as described above. Additional film-forming polymers that may be suitable for use with the present invention, alone or in combination with other polymers, include ethylene vinyl acetate, ethylene ethyl acrylate, ethylene acrylic acid, ethylene methyl acrylate, ethylene normal butyl acrylate, nylon, ethylene vinyl alcohol, polystyrene, polyurethane, and so forth.

The thickness of the skin layer(s) is generally selected so as not to substantially impair the elastomeric properties of the film. To this end, each skin layer may separately comprise from about 0.5% to about 15% of the total thickness of the film, and in some embodiments from about 1% to about 10% of the total thickness of the film. For instance, each skin layer may have a thickness of from about 0.1 to about 10 micrometers, in some embodiments from about 0.5 to about 5 micrometers, and in some embodiments, from about 1 to about 2.5 micrometers. Likewise, the base layer may have a thickness of from about from about 1 to about 40 micrometers, in some embodiments from about 2 to about 25 micrometers, and in some embodiments, from about 5 to about 20 micrometers.

Any known technique may be used to form a film from the compounded material, including blowing, casting, flat die extruding, etc. In one particular embodiment, the film may be formed by a blown process in which a gas (e.g., air) is used to expand a bubble of the extruded polymer blend through an annular die. The bubble is then collapsed and collected in flat film form. Processes for producing blown films are described, for instance, in U.S. Pat. No. 3,354,506 to Raley; U.S. Pat. No. 3,650,649 to Schippers; and U.S. Pat. No. 3,801,429 to Schrenk et al., as well as U.S. Patent Application Publication Nos. 2005/0245162 to McCormack, et al. and 2003/0068951 to Boggs, et al., all of which are incorporated herein in their entirety by reference thereto for all purposes.

Although not required, the film may be stretched to improve its properties. For example, the film may be drawn by rolls rotating at different speeds of rotation so that the sheet is stretched to the desired draw ratio in the longitudinal direction (machine direction). In addition, the uniaxially stretched film may also be oriented in the cross-machine direction to form a "biaxially stretched" film. For example, the film may be clamped at its lateral edges by chain clips and conveyed into a tenter oven. In the tenter oven, the film may be drawn in the cross-machine direction to the desired draw ratio by chain clips diverged in their forward travel. Various parameters of a stretching operation may be selectively controlled, including the draw ratio, stretching temperature, and so forth. In some embodiments, for example, the film is stretched in the machine direction at a stretch ratio of from about 1.5 to about 7.0, in some embodiments from about 1.8 to about 5.0, and in some embodiments, from about 2.0 to about 4.5. The stretch ratio may be determined by dividing the length of the stretched film by its length before stretching. The stretch ratio may also be approximately the same as the draw ratio, which may be determined by dividing the linear speed of the film upon stretching (e.g., speed of the nip rolls) by the linear speed at which the film is formed (e.g., speed of casting rolls or blown nip rolls). The orientation temperature profile is also chosen to deliver the desired shrink mechanical properties, such as shrink tension and shrink percentage. More specifically, the orientation temperature is less than the melting temperature of the semi-crystalline polyolefin. For example, the film may be stretched at a temperature from about 15° C. to about 50° C., in some embodiments from about 25° C. to about 40° C., and in some embodiments, from about 30° C. to about 40° C. Preferably, the film is "cold drawn", i.e., stretched without the application of external heat (e.g., heated rolls), to improve latent elasticity.

The properties of the resulting latent elastic film may generally vary as desired. For instance, prior to stretching, the film typically has a basis weight of from about 40 to about 250 grams per square meter, and in some embodiments, from about 60 to about 200 grams per square meter. Upon stretching, the film typically has a basis weight of from about 25 to about 150 grams per square meter or less, and in some embodiments, from about 50 to about 100 grams per square meter. The stretched film may also have a total thickness of from about 1 to about 100 micrometers, in some embodiments, from about 10 to about 80 micrometers, and in some embodiments, from about 20 to about 60 micrometers.

II. Nonwoven Web Facing

Although not required, one or more nonwoven web facings may be laminated to the latent elastic film prior to incorporation into the absorbent article to reduce the coefficient of friction and enhance the cloth-like feel of its surface. Exemplary polymers for use in forming nonwoven web facings may include, for instance, polyolefins, e.g., polyethylene, polypropylene, polybutylene, etc.; polytetrafluoroethylene; polyesters, e.g., polyethylene terephthalate and so forth; polyvinyl acetate; polyvinyl chloride acetate; polyvinyl butyral; acrylic resins, e.g., polyacrylate, polymethylacrylate, polymethylmethacrylate, and so forth; polyamides, e.g., nylon; polyvinyl chloride; polyvinylidene chloride; polystyrene; polyvinyl alcohol; polyurethanes; polylactic acid; copolymers thereof; and so forth. If desired, biodegradable polymers, such as those described above, may also be employed. Synthetic or natural cellulosic polymers may also be used, including but not limited to, cellulosic esters; cellulosic ethers; cellulosic nitrates; cellulosic acetates; cellulosic acetate butyrates; ethyl cellulose; regenerated celluloses, such as viscose, rayon, and so forth. It should be noted that the polymer(s) may also contain other additives, such as processing aids or treatment compositions to impart desired properties to the fibers, residual amounts of solvents, pigments or colorants, and so forth.

Monocomponent and/or multicomponent fibers may be used to form the nonwoven web facing. Monocomponent fibers are generally formed from a polymer or blend of polymers extruded from a single extruder. Multicomponent fibers are generally formed from two or more polymers (e.g., bicomponent fibers) extruded from separate extruders. The polymers may be arranged in substantially constantly positioned distinct zones across the cross-section of the fibers. The components may be arranged in any desired configuration, such as sheath-core, side-by-side, pie, island-in-the-sea, three island, bull's eye, or various other arrangements known in the art. Various methods for forming multicomponent fibers are described in U.S. Pat. No. 4,789,592 to Taniguchi et al. and U.S. Pat. No. 5,336,552 to Strack, et al., U.S. Pat. No. 5,108,820 to Kaneko, et al., U.S. Pat. No. 4,795,668 to Kruege, et al., U.S. Pat. No. 5,382,400 to Pike, et al., U.S. Pat. No. 5,336,552 to Strack, et al., and U.S. Pat. No. 6,200,669 to Marmon, et al., which are incorporated herein in their entirety by reference thereto for all purposes. Multicomponent fibers having various irregular shapes may also be formed, such as described in U.S. Pat. No. 5,277,976 to Hogle, et al., U.S. Pat. No. 5,162,074 to Hills, U.S. Pat. No. 5,466,410 to Hills, U.S. Pat. No. 5,069,970 to Largman, et al., and U.S. Pat. No. 5,057,368 to Largman, et al., which are incorporated herein in their entirety by reference thereto for all purposes.

Although any combination of polymers may be used, the polymers of the multicomponent fibers are typically made from thermoplastic materials with different glass transition or melting temperatures where a first component (e.g., sheath) melts at a temperature lower than a second component (e.g., core). Softening or melting of the first polymer component of the multicomponent fiber allows the multicomponent fibers to form a tacky skeletal structure, which upon cooling, stabilizes the fibrous structure. For example, the multicomponent fibers may have from about 5% to about 80%, and in some embodiments, from about 10% to about 60% by weight of the low melting polymer. Further, the multicomponent fibers may have from about 95% to about 20%, and in some embodiments, from about 90% to about 40%, by weight of the high melting polymer. Some examples of known sheath-core bicomponent fibers available from KoSa Inc. of Charlotte, N.C. under the designations T-255 and T-256, both of which use a polyolefin sheath, or T-254, which has a low melt co-polyester sheath. Still other known bicomponent fibers that may be used include those available from the Chisso Corporation of Moriyama, Japan or Fibervisions LLC of Wilmington, Del.

Fibers of any desired length may be employed, such as staple fibers, continuous fibers, etc. In one particular embodiment, for example, staple fibers may be used that have a fiber length in the range of from about 1 to about 150 millimeters, in some embodiments from about 5 to about 50 millimeters, in some embodiments from about 10 to about 40 millimeters, and in some embodiments, from about 10 to about 25 millimeters. Although not required, carding techniques may be employed to form fibrous layers with staple fibers as is well known in the art. For example, fibers may be formed into a carded web by placing bales of the fibers into a picker that separates the fibers. Next, the fibers are sent through a combing or carding unit that further breaks apart and aligns the fibers in the machine direction so as to form a machine direction-oriented fibrous nonwoven web. The carded web may then be bonded using known techniques to form a bonded carded nonwoven web.

If desired, the nonwoven web facing used to form the nonwoven composite may have a multi-layer structure. Suitable multi-layered materials may include, for instance, spunbond/meltblown/spunbond (SMS) laminates and spunbond/meltblown (SM) laminates. Various examples of suitable SMS laminates are described in U.S. Pat. No. 4,041,203 to Brock et al.; U.S. Pat. No. 5,213,881 to Timmons, et al.; U.S. Pat. No. 5,464,688 to Timmons, et al.; U.S. Pat. No. 4,374,888 to Bornslaeger; U.S. Pat. No. 5,169,706 to Collier, et al.; and U.S. Pat. No. 4,766,029 to Brock et al., which are incorporated herein in their entirety by reference thereto for all purposes. In addition, commercially available SMS laminates may be obtained from Kimberly-Clark Corporation under the designations Spunguard® and Evolution®.

Another example of a multi-layered structure is a spunbond web produced on a multiple spin bank machine in which a spin bank deposits fibers over a layer of fibers deposited from a previous spin bank. Such an individual spunbond nonwoven web may also be thought of as a multi-layered structure. In this situation, the various layers of deposited fibers in the nonwoven web may be the same, or they may be different in basis weight and/or in terms of the composition, type, size, level of crimp, and/or shape of the fibers produced. As another example, a single nonwoven web may be provided as two or more individually produced layers of a spunbond web, a carded web, etc., which have been bonded together to form the nonwoven web. These individually produced layers may differ in terms of production method, basis weight, composition, and fibers as discussed above.

A nonwoven web facing may also contain an additional fibrous component such that it is considered a composite. For example, a nonwoven web may be entangled with another fibrous component using any of a variety of entanglement techniques known in the art (e.g., hydraulic, air, mechanical, etc.). In one embodiment, the nonwoven web is integrally entangled with cellulosic fibers using hydraulic entanglement. A typical hydraulic entangling process utilizes high pressure jet streams of water to entangle fibers to form a highly entangled consolidated fibrous structure, e.g., a nonwoven web. Hydraulically entangled nonwoven webs of staple length and continuous fibers are disclosed, for example, in U.S. Pat. No. 3,494,821 to Evans and U.S. Pat. No. 4,144,370 to Boulton, which are incorporated herein in their entirety by reference thereto for all purposes. Hydraulically entangled composite nonwoven webs of a continuous fiber nonwoven web and a pulp layer are disclosed, for example, in U.S. Pat. No. 5,284,703 to Everhart, et al. and U.S. Pat. No. 6,315,864 to Anderson, et al., which are incorporated herein in their entirety by reference thereto for all purposes. The fibrous component of the composite may contain any desired amount of the resulting substrate. The fibrous component may contain greater than about 50% by weight of the composite, and in some embodiments, from about 60% to about 90% by weight of the composite. Likewise, the nonwoven web may contain less than about 50% by weight of the composite, and in some embodiments, from about 10% to about 40% by weight of the composite.

The nonwoven web facing may be necked in one or more directions prior to lamination to the film of the present invention. Suitable necking techniques are described in U.S. Pat. Nos. 5,336,545, 5,226,992, 4,981,747 and 4,965,122 to Morman, as well as U.S. Patent Application Publication No. 2004/0121687 to Morman, et al. Alternatively, the nonwoven web may remain relatively inextensible in at least one direction prior to lamination to the film. In such embodiments, the nonwoven web may be optionally stretched in one or more directions subsequent to lamination to the film.

The basis weight of the nonwoven web facing may generally vary, such as from about 5 grams per square meter ("gsm") to 120 gsm, in some embodiments from about 8 gsm to about 70 gsm, and in some embodiments, from about 10 gsm to about 35 gsm. When multiple nonwoven web facings, such materials may have the same or different basis weights.

Any of a variety of techniques may be employed to laminate a nonwoven facing to the latent elastic film of the present invention, including adhesive bonding; thermal bonding; ultrasonic bonding; microwave bonding; extrusion coating; and so forth. In one particular embodiment, nip rolls apply a pressure to the film and nonwoven facing(s) to thermally bond the materials together. The rolls may be smooth and/or contain a plurality of raised bonding elements. Adhesives may also be employed, such as Rextac 2730 and 2723 available from Huntsman Polymers of Houston, Tex., as well as adhesives available from Bostik Findley, Inc, of Wauwatosa, Wis. The type and basis weight of the adhesive used will be determined on the elastic attributes desired in the final composite and end use. For instance, the basis weight of the adhesive may be from about 1.0 to about 3.0 gsm. The adhesive may be applied to the nonwoven web facings and/or the elastic film prior to lamination using any known technique, such as slot or melt spray adhesive systems. During lamination, the film may in a stretched or relaxed condition depending on the desired properties of the resulting composite.

Various additional potential processing and/or finishing steps known in the art, such as slitting, treating, printing graphics, etc., may be performed without departing from the spirit and scope of the invention. For instance, the composite may optionally be mechanically stretched in the cross-machine and/or machine directions to enhance extensibility. In one embodiment, the composite may be coursed through two or more rolls that have grooves in the CD and/or MD directions. Such grooved satellite/anvil roll arrangements are described in U.S. Patent Application Publication Nos. 2004/0110442 to Rhim, et al. and 2006/0151914 to Gerndt, et al., which are incorporated herein in their entirety by reference thereto for all purposes. For instance, the laminate may be coursed through two or more rolls that have grooves in the CD and/or MD directions. The grooved rolls may be constructed of steel or other hard material (such as a hard rubber). If desired, heat may be applied by any suitable method known in the art, such as heated air, infrared heaters, heated nipped rolls, or partial wrapping of the laminate around one or more heated rolls or steam canisters, etc. Heat may also be applied to the grooved rolls themselves. It should also be understood that other grooved roll arrangement are equally suitable, such as two grooved rolls positioned immediately adjacent to one another. Besides grooved rolls, other techniques may also be used to mechanically stretch the composite in one or more directions. For example, the composite may be passed through a tenter frame that stretches the composite. Such tenter frames are well known in the art and described, for instance, in U.S. Patent Application Publication No. 2004/0121687 to Morman, et al. The composite may also be necked. Suitable techniques necking techniques are described in U.S. Pat. Nos. 5,336,545, 5,226,992, 4,981,747 and 4,965,122 to Morman, as well as U.S. Patent Application Publication No. 2004/0121687 to Morman, et al., all of which are incorporated herein in their entirety by reference thereto for all purposes.

III. Absorbent Article

Regardless of its particular construction and/or whether it is laminated to one or more facings, the latent elastic film of the present invention is incorporated into an absorbent article. Because the latent elastic film of the present invention is not highly elastic prior to crosslinking and is thus more dimensionally stable, it has a greater dimensional stability than highly elastic materials. This allows enhanced processing efficiencies to be realized when incorporating the film into the absorbent article. For example, the film need not be maintained in a mechanically stretched condition during attachment to other components of the absorbent article. This allows for greater freedom in the location and manner in which the components are attached together.

The absorbent article normally includes a substantially liquid-impermeable layer (e.g., outer cover), a liquid-permeable layer (e.g., bodyside liner, surge layer, etc.), an absorbent core, and various other optional components. As is well known in the art, a variety of absorbent article components may possess elastic characteristics, such as waistbands, leg/cuff gasketing, containment flaps, ears, side panels, outer covers, and so forth. The latent elastic film of the present invention may be employed for use in any of such components.

Referring to FIG. 1, for example, one embodiment of a disposable diaper 250 is shown that generally defines a front waist section 255, a rear waist section 260, and an intermediate section 265 that interconnects the front and rear waist sections. The front and rear waist sections 255 and 260 include the general portions of the diaper which are constructed to extend substantially over the wearer's front and rear abdominal regions, respectively, during use. The intermediate section 265 of the diaper includes the general portion of the diaper that is constructed to extend through the wearer's crotch region between the legs. Thus, the intermediate section 265 is an area where repeated liquid surges typically occur in the diaper.

The diaper 250 includes, without limitation, an outer cover, or backsheet 270, a liquid permeable bodyside liner, or topsheet, 275 positioned in facing relation with the backsheet 270, and an absorbent core body, or liquid retention structure, 280, such as an absorbent pad, which is located between the backsheet 270 and the topsheet 275. The backsheet 270 defines a length, or longitudinal direction 286, and a width, or lateral direction 285 which, in the illustrated embodiment, coincide with the length and width of the diaper 250. The liquid retention structure 280 generally has a length and width that are less than the length and width of the backsheet 270, respectively. Thus, marginal portions of the diaper 250, such as marginal sections of the backsheet 270 may extend past the terminal edges of the liquid retention structure 280. In the illustrated embodiments, for example, the backsheet 270 extends outwardly beyond the terminal marginal edges of the liquid retention structure 280 to form side margins and end margins of the diaper 250. The topsheet 275 is generally coextensive with the backsheet 270 but may optionally cover an area that is larger or smaller than the area of the backsheet 270, as desired.

To provide improved fit and to help reduce leakage of body exudates from the diaper 250, the diaper side margins and end margins may be elasticized with suitable elastic members, as further explained below. For example, as representatively illustrated in FIG. 1, the diaper 250 may include leg/cuff gasketing 290 constructed to operably tension the side margins of the diaper 250 and closely fit around the legs of the wearer to reduce leakage and provide improved comfort and appearance. Waistbands 295 are employed that provide a resilient, comfortably close fit around the waist of the wearer. The latent elastic film of the present invention is suitable for use as the leg/cuff gasketing 290 and/or waistbands 295. Exemplary of such materials are laminate sheets that either comprise or are adhered to the backsheet, such that elastic constrictive forces are imparted to the backsheet 270.

As is known, fastening means, such as hook and loop fasteners, may be employed to secure the diaper 250 on a wearer. Alternatively, other fastening means, such as buttons, pins, snaps, adhesive tape fasteners, cohesives, fabric-and-loop fasteners, or the like, may be employed. In the illustrated embodiment, the diaper 250 includes a pair of side panels 300 (or ears) to which the fasteners 302, indicated as the hook portion of a hook and loop fastener, are attached. Generally, the side panels 300 are attached to the side edges of the diaper in one of the waist sections 255, 260 and extend laterally outward therefrom. The side panels 300 may contain the latent elastic film of the present invention. Examples of absorbent articles that include side panels and selectively configured fastener tabs are described in PCT Patent Application WO 95/16425 to Roessler; U.S. Pat. No. 5,399,219 to Roessler et al.; U.S. Pat. No. 5,540,796 to Fries; and U.S. Pat. No. 5,595,618 to Fries, each of which is incorporated herein in its entirety by reference thereto for all purposes.

The diaper 250 may also include a surge management layer 305, located between the topsheet 275 and the liquid retention structure 280, to rapidly accept fluid exudates and distribute the fluid exudates to the liquid retention structure 280 within the diaper 250. The diaper 250 may further include a ventilation layer (not illustrated), also called a spacer, or spacer layer, located between the liquid retention structure 280 and the backsheet 270 to insulate the backsheet 270 from the liquid retention structure 280 to reduce the dampness of the garment at the exterior surface of a breathable outer cover, or backsheet, 270. Examples of suitable surge management layers 305 are described in U.S. Pat. No. 5,486,166 to Bishop and U.S. Pat. No. 5,490,846 to Ellis.

As representatively illustrated in FIG. 1, the disposable diaper 250 may also include a pair of containment flaps 310 which are configured to provide a barrier to the lateral flow of body exudates. The containment flaps 310 may be located along the laterally opposed side edges of the diaper adjacent the side edges of the liquid retention structure 280. Each containment flap 310 typically defines an unattached edge that is configured to maintain an upright, perpendicular configuration in at least the intermediate section 265 of the diaper 250 to form a seal against the wearer's body. The containment flaps 310 may extend longitudinally along the entire length of the liquid retention structure 280 or may only extend partially along the length of the liquid retention structure. When the containment flaps 310 are shorter in length than the liquid retention structure 280, the containment flaps 310 can be selectively positioned anywhere along the side edges of the diaper 250 in the intermediate section 265. Such containment flaps 310 are generally well known to those skilled in the art. For example, suitable constructions and arrangements for containment flaps 310 are described in U.S. Pat. No. 4,704,116 to Enloe. The latent elastic film of the present invention may also be employed in such containment flaps 310.

The diaper 250 may be of various suitable shapes. For example, the diaper may have an overall rectangular shape, T-shape or an approximately hour-glass shape. In the shown embodiment, the diaper 250 has a generally I-shape. Other suitable components which may be incorporated on absorbent articles of the present invention may include waist flaps and the like which are generally known to those skilled in the art. Examples of diaper configurations suitable for use in connection with the latent elastic films of the present invention that may include other components suitable for use on diapers are described in U.S. Pat. No. 4,798,603 to Meyer, et al.; U.S. Pat. No. 5,176,668 to Bernardin; U.S. Pat. No. 5,176,672 to Bruemmer, et al.; U.S. Pat. No. 5,192,606 to Proxmire, et al.; and U.S. Pat. No. 5,509,915 to Hanson, et al., which are incorporated herein in their entirety by reference thereto for all purposes.

The various regions and/or components of the diaper 250 may be assembled together using any known attachment mechanism, such as adhesive, ultrasonic, thermal bonds, etc. Suitable adhesives may include, for instance, hot melt adhesives, pressure-sensitive adhesives, and so forth. When utilized, the adhesive may be applied as a uniform layer, a patterned layer, a sprayed pattern, or any of separate lines, swirls or dots. In the illustrated embodiment, for example, the topsheet 275 and backsheet 270 may be assembled to each other and to the liquid retention structure 280 with lines of adhesive, such as a hot melt, pressure-sensitive adhesive. Similarly, other diaper components, such as the leg/cuff gasketing 290, waistband 295, fastening members 302, and surge layer 305 may be assembled into the article by employing the above-identified attachment mechanisms.

Although various configurations of a diaper have been described above, it should be understood that other diaper and absorbent article configurations are also included within the scope of the present invention. In addition, the present invention is by no means limited to diapers. In fact, several examples of absorbent articles are described in U.S. Pat. No. 5,649,916 to DiPalma, et al.; U.S. Pat. No. 6,110,158 to Kielpikowski; U.S. Pat. No. 6,663,611 to Blaney, et al., which are incorporated herein in their entirety by reference thereto for all purposes. Further, other examples of personal care products that may incorporate such materials are training pants (such as in side panel materials) and feminine care products. By way of illustration only, training pants suitable for use with the present invention and various materials and methods for constructing the training pants are disclosed in U.S. Pat. No. 6,761,711 to Fletcher et al.; U.S. Pat. No. 4,940,464 to Van Gompel et al.; U.S. Pat. No. 5,766,389 to Brandon et al.; and U.S. Pat. No. 6,645,190 to Olson et al., which are incorporated herein in their entirety by reference thereto for all purposes.

Upon incorporation into the absorbent article, the semi-crystalline polyolefin(s) of the latent elastic film is crosslinked in accordance with the present invention to provide the polymer with a sufficient degree of "memory." That is, the crosslinked polymer chains may straighten when stretched, but ultimately return to their original position once the stress is removed because the crosslinks prevent the individual chains from sliding past each other. Crosslinking is generally achieved through the formation of free radicals (unpaired electrons) that link together to form a plurality of carbon-carbon covalent bonds. These bonds create a three-dimensional network from the original linear polymer chains.

Free radical formation is generally induced in the present invention through electromagnetic radiation, either alone or in the presence of pro-rad additives, such as described above. More specifically, crosslinking is induced by subjecting at least a portion of the absorbent article to electromagnetic radiation. The entire absorbent article may be subjected to radiation, or simply one or more zones of the article that contain the latent elastic film of the present invention. Some suitable examples of electromagnetic radiation that may be used in the present invention include, but are not limited to, ultraviolet light, electron beam radiation, natural and artificial radio isotopes (e.g., $\alpha$, $\beta$, and $\gamma$ rays), x-rays, neutron beams, positively-charged beams, laser beams, and so forth. Electron beam radiation, for instance, involves the production of accelerated electrons by an electron beam device. Electron beam devices are generally well known in the art. For instance, in one embodiment, an electron beam device may be used that is available from Energy Sciences, Inc., of Woburn, Mass. under the name "Microbeam LV." Other examples of suitable electron beam devices are described in U.S. Pat. No. 5,003,178 to Livesay; U.S. Pat. No. 5,962,995 to Avnery; U.S. Pat. No. 6,407,492 to Avnery, et al., which are incorporated herein in their entirety by reference thereto for all purposes.

When supplying electromagnetic radiation, it is generally desired to selectively control various parameters of the radiation to enhance the degree of crosslinking of the semi-crystalline polyolefin(s). For example, one parameter that may be controlled is the wavelength $\lambda$ of the electromagnetic radiation. Specifically, the wavelength $\lambda$ of the electromagnetic radiation varies for different types of radiation of the electromagnetic radiation spectrum. Although not required, the wavelength $\lambda$ of the electromagnetic radiation used in the present invention is generally about 1000 nanometers or less, in some embodiments about 100 nanometers or less, and in some embodiments, about 1 nanometer or less. Electron beam radiation, for instance, typically has a wavelength $\lambda$ of about 1 nanometer or less. Besides selecting the particular wavelength $\lambda$ of the electromagnetic radiation, other parameters may also be selected to optimize the degree of crosslinking. For example, higher dosage and energy levels of radiation will typically result in the a higher degree of crosslinking; however, it is generally desired that the materials not be "overexposed" to radiation. Such overexposure may result in an unwanted level of product degradation. Thus, in some embodiments, the dosage may range from about 1 megarad (Mrad) to about 30 Mrads, in some embodiments, from about 3 Mrads to about 25 Mrads, and in some embodiments, from about 5 to about 15 Mrads. In addition, the energy level may range from about 0.05 megaelectron volts (MeV) to about 600 MeV.

It should be understood, however, that the actual dosage and/or energy level required depends on the type of polymers and electromagnetic radiation. Specifically, certain types of polymers may tend to form a lesser or greater number of crosslinks, which will influence the dosage and energy of the radiation utilized. Likewise, certain types of electromagnetic radiation may be less effective in crosslinking the polymer, and thus may be utilized at a higher dosage and/or energy level. For instance, electromagnetic radiation that has a relatively high wavelength (lower frequency) may be less efficient in crosslinking the polymer than electromagnetic radiation having a relatively low wavelength (higher frequency). Accordingly, in such instances, the desired dosage and/or energy level may be increased to achieve the desired degree of crosslinking.

In addition to forming a three-dimensional elastomer network, crosslinking may also provide a variety of other benefits to the semi-crystalline polyolefin. Lotions used to enhance skin care, for instance, may contain petroleum-based components and/or other components that are compatible with thermoplastics polymers. If the lotions come into sufficient contact with an elastic material, its performance may be significantly degraded. In this regard, the crosslinked semi-crystalline polyolefin(s) may exhibit improvement in lotion degradation resistance. Furthermore, certain types of crosslinking techniques (e.g., electron beam radiation) may generate sufficient heat to effectively "heat shrink" the film and provide it with additional latent stretchability. For instance, the film may be heated at or above the softening temperature of the polyolefin to soften the crystalline domains and allow the chains to return to their unoriented state. As a result, the elastic film may be extended and recover from its unoriented state.

If desired, a separate heat activation step may be employed to further enhance the heat shrinkage performance of the film. Such an additional heat activation step may occur before and/or after crosslinking. Preferably, however, heat activation occurs before crosslinking to achieve the full shrinkage potential of the film. Heat activation may be accomplished at temperatures of from about 50° C. to about 100° C., in some embodiments from about 60° C. to about 90° C., and in some embodiments, from about 70° C. to about 80° C. Any of a variety of techniques may be used to apply heat to the film, such as heated rolls, oven heating, and so forth. For example, the latent elastic film may be activated through the application of heat during formation of the absorbent article, such as during the curing process for an adhesive used to attach together various components of the product. Regardless of the particular manner in which it is activated, the heat shrinkage performance of the film, which is a measure of recoverable deformation upon activation, may be about 5% or more, in some embodiments about 10% or more, and in some embodiments, about 20% or more. As described in the "Test Methods" below, heat shrinkage is determined by heating the material in water at 160° F. for 30 seconds to 1 minute. Alternatively, shrinkage may be determined using ASTM D2838-02.

The present invention may be better understood with reference to the following example.

Test Methods

% Heat Shrinkage

To measure heat-activated retraction, marks spaced 100 millimeters apart are placed on the material while it is still under tension on the roll. The material is then released from tension on the roll and a length of material containing the marks is cut from the roll. Immediately after releasing the material and cutting it, the distance between the marks is measured again to determine the initial length (Before Heated Retraction Length or "BHRL"). The material is then submerged in water (160° F.) for at least 30 seconds, but no more than 1 minute. Thereafter, the distance between the marks is again measured (After Heated Retraction Length or "AHRL"). The percent shrinkage is indicative of the latent elasticity of the material and is calculated by the following equation:

% shrinkage=100*(BHRL−AHRL)/BHRL

Three measurements are averaged for each sample to be tested. The measurements are taken at ambient conditions.

Cycle Testing

The materials were tested using a cyclical testing procedure to determine load loss and percent set. In particular, 1-cycle testing was utilized to 150% defined elongation. For this test, the sample size was 3 inches in the cross-machine direction by 6 inches in the machine direction. The grip size was 3 inches in width. The grip separation was 4.5 inches. The samples were loaded such that the machine direction of the sample was in the vertical direction. A preload of approximately 10 to 15 grams was set. The test pulled the sample to 150% elongation at a speed of 20 inches per minute, and then immediately (without pause) returned to the zero at a speed of 20 inches per minute. The test reported percent set and percent hysteresis. The "percent set" is the measure of the amount of the material stretched from its original length after being cycled (the immediate deformation following the cycle test). The percent set is where the retraction curve of a cycle crosses the elongation axis. The remaining strain after the removal of the applied stress is measured as the percent set. The hysteresis value is the loss of energy during the cyclic loading. The testing was done on a Sintech Corp. constant rate of extension tester 2/S with a Renew MTS mongoose box (controller) using TESTWORKS 4.07b software (Sintech Corp, of Cary, N.C.). The tests were conducted at ambient conditions.

Stress Relaxation

Stress relaxation is defined as the force required to hold a given elongation constant over a period of time and is generally indicative of the dimensional stability of a material. Testing was performed by clamping a test specimen (3" in width) between the jaws of a Sintech extension tester at a 3" grip to grip distance. The sample and the grip fixtures were enclosed in an environmental chamber. The sample, after clamping, was equilibrated at 100° F. for 3 minutes. The sample was then elongated to a final constant elongation of 4.5 inches (50% elongation) at a cross-head displacement speed of 20 inches per minute. The load required to maintain the 50% elongation as a function of time was monitored. The slope of the stress curve and the percent load loss were reported. The percent load loss was calculated by subtracting the load at 12 hours from the initial load, dividing by the initial load, and then multiplying the ratio by 100. The testing was done on a Sintech Corp. constant rate of extension tester 2/S with a Renew MTS mongoose box (controller) using TESTWORKS 4.07b software (Sintech Corp, of Cary, N.C.).

Example

A polymer blend was initially formed from varying percentages of VECTOR™ 7400 (Dexco Polymers), EXACT™ 5361 (Exxon Mobil Chemical Co.), DP 2232 and 2231, and CN2303. EXACT™ 5361 is a metallocene-catalyzed polyethylene plastomer having a density of 0.86 grams per cubic centimeter, a peak melting temperature of 36° C., and a melt index of 3.0 grams per 10 minutes (190° C., 2.16 kg). VECTOR™ 7400 (Dexco Polymers) is a linear, pure SBS triblock copolymer extended with 33% mineral oil. It is a medium styrene, low viscosity product containing no residual diblock. CN2303 (pro-rad additive) is a hyperbranched polyester acrylate oligomer available from Sartomer. DP2231 and DP2232 are styrene-butadiene-styrene ("SBS") block copolymers obtained from Dexco Polymers. The polymers and any additives were introduced into the hopper of a Leistritz twin screw co-rotating multi-mode extruder (Model Mic 27GL/40D) equipped with 27 mm screws at a 40:1 L/D. The extruder is an electrically resistance heated extruder with water cooling, and contains 9 barrel and 2 auxiliary barrel heating sections. The extruder was fitted with two "pineapple" mixing elements based on the principle of distributive mixing in the middle and end zones. The extruder was also directly fitted with a 10" coat-hanger type film die that can be heated. The film was extruded at a back pressure of about 500 to 1000 psi at 300 rpm at a feed rate of approximately 8 lbs/hr. The extruded film was then cast onto a chill roll and wound onto a take-up roll. The extrusion parameters for the samples are set forth below in Table 1.

TABLE 1

| | Extrusion Parameters | | | | |
| --- | --- | --- | --- | --- | --- |
| | Sample Nos. | | | | |
| | 1, 6, & 11 | 2, 7, & 12 | 3, 8, & 13 | 4, 9, & 14 | 5, 10, & 15 |
| Exact 5361 | 100 | 75 | 75 | 50 | 98 |
| Dexco 2232 | | | 25 | 25 | |

TABLE 1-continued

Extrusion Parameters

| | Sample Nos. | | | | |
|---|---|---|---|---|---|
| | 1, 6, & 11 | 2, 7, & 12 | 3, 8, & 13 | 4, 9, & 14 | 5, 10, & 15 |
| Dexco 2231 | | | | 25 | |
| Vector 7400 | | 25 | | | |
| CN2303 | | | | | 2 |
| Inputs | | | | | |
| Feed Rate (lb/hr) | 8 | 8 | 8 | 8 | 8 |
| Screw Speed (rpm) | 200 | 200 | 200 | 300 | 300 |
| Temperatures (° C.) | | | | | |
| Zone 1 | 180 | 180 | 180 | 152 | 152 |
| Zone 2 | 189 | 189 | 189 | 155 | 155 |
| Zone 3 | 196 | 196 | 196 | 155 | 155 |
| Zone 4 | 201 | 201 | 201 | 155 | 155 |
| Zone 5 | 196 | 196 | 196 | 155 | 155 |
| Zone 6 | 191 | 191 | 191 | 155 | 155 |
| Zone 7 | 187 | 187 | 187 | 155 | 155 |
| Zone 8 | 186 | 186 | 186 | 155 | 155 |
| Zone 9 | 185 | 185 | 185 | 160 | 160 |
| Zone 10 | 185 | 185 | 185 | 165 | 165 |
| Zone 11 | 195 | 195 | 195 | 165 | 165 |
| Torque (lbs) | 25 | 25 | 25 | 20 | 25 |
| Winder Speed (fpm) | 13 | 13 | 10 | 7 | 13 |
| Chill Roll Speed (fpm) | 13 | 13 | 10 | 7 | 13 |
| Outputs | | | | | |
| Die Pressure (psi) | 670 | 500 | 720 | 870 | 980 |
| Film Thickness (mil) | 3 | 3 | 3 | 6 | 3 |
| Film Thickness (gsm) | 20 | 20 | 20 | 40 | 20 |

Once formed, several of the film samples were subjected to electron beam radiation using Energy Sciences' Pilot line equipment, which operated at a Voltage range from 80 kV to 200 kV, at a depth of 150 microns, density of 1 g/cc, and a dosage range of 1-9 Mrads depending on speed. The samples had an approximate dimension of 10"×11" and were placed on a carrier film that unwinds at one end and winds in the other end. Exposed samples were collected and run a second or third time depending on the dosage required. The materials were tested for shrinkage and elastomeric performance (before and after heat activation) as described above. The results are set forth below in Tables 2 and 3.

TABLE 2

| | Film Sample Construction | | | | | |
|---|---|---|---|---|---|---|
| Sample | Exact ™ 5361 (wt. %) | VECTOR ™ 7400 (wt. %) | DPR 2232 (wt. %) | DPR 2231 (wt. %) | CN2303 (wt. %) | E-Beam Radiation Level (Mrads) |
| 1 | 100 | — | — | — | — | — |
| 2 | 75 | 25 | — | — | — | — |
| 3 | 75 | — | 25 | — | — | — |
| 4 | 50 | — | 25 | 25 | — | — |
| 5 | 98 | — | — | — | 2 | — |
| 6 | 100 | — | — | — | — | 10 |
| 7 | 75 | 25 | — | — | — | 10 |
| 8 | 75 | — | 25 | — | — | 10 |
| 9 | 50 | — | 25 | 25 | — | 10 |
| 10 | 98 | — | — | — | 2 | 10 |
| 11 | 100 | — | — | — | — | 15 |
| 12 | 75 | 25 | — | — | — | 15 |
| 13 | 75 | — | 25 | — | — | 15 |
| 14 | 50 | — | 25 | 25 | — | 15 |
| 15 | 98 | — | — | — | 2 | 15 |

TABLE 3

| | | | Before Heat Activation | | | | After Heat activation | | | |
| | | | Mechanical | | Stress Relaxation | | Mechanical | | Stress Relaxation | |
| Sample | Before Heat Activation Shrinkage % | After Heat Activation Shrinkage % | % Hyst | % Set | Slope | Load Loss (%) | % Hyst | % Set | Slope | Load Loss (%) |
|---|---|---|---|---|---|---|---|---|---|---|
| 1 | — | 53.0 | 43 | 19 | −0.11 | 64 | 43 | 19 | −0.06 | 54 |
| 2 | — | 33.0 | 51 | 29 | −0.11 | 58 | 51 | 29 | −0.11 | 72 |
| 3 | — | 44.0 | 44 | 22 | −0.11 | 63 | 44 | 22 | −0.13 | 76 |
| 4 | — | 47.0 | 43 | 18 | −0.14 | 62 | 40 | 21 | −0.14 | 74 |
| 5 | — | 37.0 | 49 | 19 | −0.03 | 60 | 55 | 21 | −0.10 | 64 |
| 6 | +4.2 | 0.0 | 39 | 19 | −0.13 | 65 | 55 | 31 | −0.06 | 39 |
| 7 | −1.0 | 1.6 | 40 | 23 | −0.08 | 54 | 41 | 18 | 0.07 | 51 |
| 8 | +4.2 | 5.1 | 41 | 16 | −0.09 | 59 | 39 | 18 | −0.07 | 54 |
| 9 | −4.5 | 9.1 | 36 | 18 | −0.09 | 53 | 46 | 25 | −0.08 | 52 |
| 10 | −7.3 | 5.2 | 46 | 23 | −0.07 | 55 | 40 | 20 | −0.10 | 63 |
| 11 | +2.8 | 7.1 | 38 | 19 | −0.03 | 35 | 52 | 28 | −0.05 | 43 |
| 12 | −2.4 | 5.4 | 44 | 26 | −0.07 | 58 | 43 | 21 | −0.06 | 53 |
| 13 | +5.5 | 1.0 | 41 | 17 | −0.07 | 51 | 38 | 18 | −0.08 | 55 |
| 14 | 0.0 | 12.7 | 46 | 23 | −0.07 | 51 | 47 | 26 | −0.08 | 56 |
| 15 | +3.0 | 11.6 | 40 | 21 | −0.06 | 55 | 39 | 19 | −0.08 | 54 |

While the invention has been described in detail with respect to the specific embodiments thereof, it will be appreciated that those skilled in the art, upon attaining an understanding of the foregoing, may readily conceive of alterations to, variations of, and equivalents to these embodiments. Accordingly, the scope of the present invention should be assessed as that of the appended claims and any equivalents thereto.

What is claimed is:

1. A method of forming an absorbent article, the method comprising:
   fastening a latent elastic film to one or more components of the article, wherein the latent elastic film comprises at least one crosslinkable semi-crystalline polyolefin having a density of about 0.91 grams per cubic centimeter or less, the semi-crystalline polyolefin constituting about 30 wt. % or more of the polymer content of the film; and
   thereafter, subjecting the absorbent article to a dosage of electromagnetic radiation sufficient to crosslink the semi-crystalline polyolefin, wherein the crosslinked semi-crystalline polyolefin is elastic.

2. The method of claim 1, wherein the semi-crystalline polyolefin has a density of from about 0.85 to about 0.89 grams per cubic centimeter.

3. The method of claim 1, wherein the semi-crystalline polyolefin is an ethylene/α-olefin copolymer, propylene/α-olefin copolymer, or a combination thereof.

4. The method of claim 1, wherein the semi-crystalline polyolefin is single-site catalyzed.

5. The method of claim 1, wherein the semi-crystalline polyolefin constitutes about 50 wt. % or more of the polymer content of the film.

6. The method of claim 1, wherein the film is laminated to at least one nonwoven web facing.

7. The method of claim 6, wherein the nonwoven web facing contains a spunbond web, meltblown web, or a combination thereof.

8. The method of claim 1, wherein the electromagnetic radiation has a wavelength of about 100 nanometers or less.

9. The method of claim 1, wherein the electromagnetic radiation has a wavelength of about 1 nanometer or less.

10. The method of claim 1, wherein the electromagnetic radiation is electron beam radiation.

11. The method of claim 1, wherein the dosage of the electromagnetic radiation is from about 1 to about 30 Megarads.

12. The method of claim 1, wherein the dosage of the electromagnetic radiation is from about 5 to about 15 Megarads.

13. The method of claim 1, further comprising heating the film to induce shrinkage.

14. The method of claim 13, wherein the film is heated at a temperature of from about 50° C. to about 100° C.

15. The method of claim 13, wherein the film exhibits heat shrinkage of about 5% or more.

16. The method of claim 13, wherein the film exhibits heat shrinkage of about 10% or more.

17. The method of claim 1, wherein an adhesive is used to fasten the film.

18. The method of claim 1, wherein the absorbent includes an absorbent core positioned between a substantially liquid-impermeable layer and a liquid-permeable layer.

19. The method of claim 18, wherein the substantially liquid-impermeable layer includes the film.

20. The method of claim 18, wherein the absorbent article further comprises a waistband, the waistband including the film.

21. The method of claim 18, wherein the absorbent article further comprises leg/cuff gasketing, the gasketing including the film.

22. The method of claim 18, wherein the absorbent article further comprises a side panel, the panel including the film.

23. A method of forming an absorbent article that includes an absorbent core positioned between a substantially liquid-impermeable layer and a liquid-permeable layer, the method comprising:
   fastening a latent elastic film to one or more components of the article, wherein the latent elastic film comprises at least one crosslinkable ethylene/α-olefin copolymer having a density of about 0.91 grams per cubic centimeter or less, the ethylene/α-olefin copolymer constituting about 30 wt. % or more of the polymer content of the film;

heating the latent elastic film at a temperature of from about 50° C. to about 100° C.; and subjecting the absorbent article to electromagnetic radiation at a dosage of about 3 to about 25 Megarads to crosslink the ethylene/α-olefin copolymer, wherein the crosslinked ethylene/α-olefin copolymer is elastic.

24. The method of claim 23, wherein the ethylene/α-olefin copolymer has a density of from about 0.85 to about 0.89 grams per cubic centimeter.

25. The method of claim 23, wherein the ethylene/α-olefin copolymer is single-site catalyzed.

26. The method of claim 23, wherein the ethylene/□-olefin copolymer constitutes about 50 wt. % or more of the polymer content of the film.

27. The method of claim 23, wherein the film is laminated to at least one nonwoven web facing.

28. The method of claim 23, wherein the electromagnetic radiation has a wavelength of about 100 nanometers or less.

29. The method of claim 23, wherein the electromagnetic radiation has a wavelength of about 1 nanometer or less.

30. The method of claim 23, wherein the electromagnetic radiation is electron beam radiation.

31. The method of claim 23, wherein the dosage of the electromagnetic radiation is from about 5 to about 15 Megarads.

32. The method of claim 23, wherein the film exhibits heat shrinkage of about 5% or more.

33. The method of claim 23, wherein the film exhibits heat shrinkage of about 10% or more.

34. The method of claim 23, wherein the substantially liquid-impermeable layer includes the film.

35. The method of claim 23, wherein the absorbent article further comprises a waistband, the waistband including the film.

36. The method of claim 23, wherein the absorbent article further comprises leg/cuff gasketing, the gasketing including the film.

37. The method of claim 23, wherein the absorbent article further comprises a side panel, the panel including the film.

38. The method of claim 23, wherein the heating occurs prior to subjecting the absorbent article to electromagnetic radiation.

* * * * *